United States Patent [19]

Pospisil

[11] Patent Number: 4,927,360
[45] Date of Patent: May 22, 1990

[54] TRIWING ORTHODONTIC BRACKET
[75] Inventor: Jirina V. Pospisil, Monrovia, Calif.
[73] Assignee: Unitek Corporation, Monrovia, Calif.
[21] Appl. No.: 187,747
[22] Filed: Apr. 29, 1988
[51] Int. Cl.⁵ .............................................. A61C 3/00
[52] U.S. Cl. ........................................... 433/8; 433/9
[58] Field of Search ..................... 433/8, 9, 10, 11, 12, 433/13, 14, 15, 16

[56] References Cited
U.S. PATENT DOCUMENTS 4,227,876 10/1980 Fogel et al. .......................... 433/11
4,322,206 3/1982 Reynolds ................................. 433/8
4,582,487 4/1986 Creekmore .............................. 433/9
4,614,497 9/1986 Kurz ........................................ 433/8

Primary Examiner—John J. Wilson
Attorney, Agent, or Firm—Donald M. Sell; Walter N. Kirn; James D. Christoff

[57] ABSTRACT

A triwing orthodontic bracket for mandibular teeth, and having a single wide occlusal tie wing of enhanced structural strength, and a pair of spaced-apart gingival tie wings which enable rotational tooth movement and simplified ligature installation.

4 Claims, 2 Drawing Sheets

FIG. 5
FIG. 6
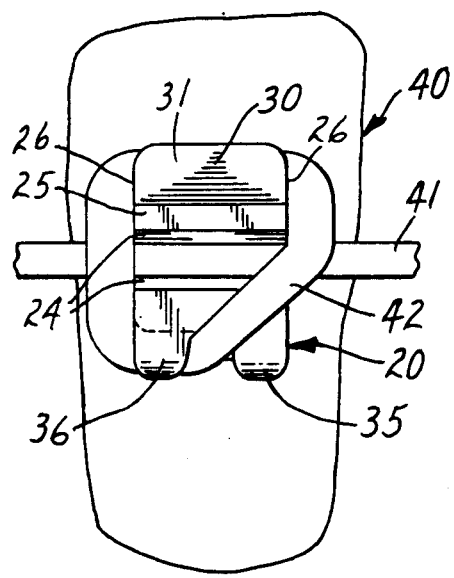
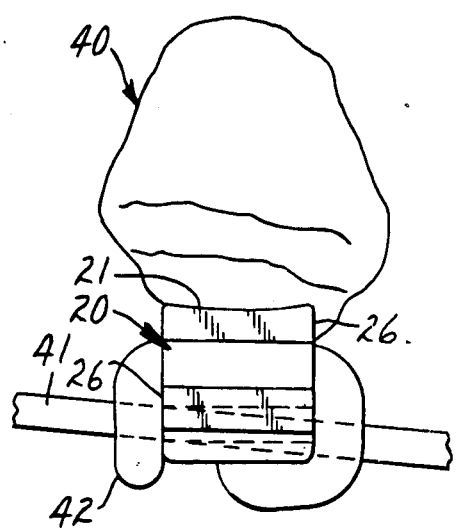

TRIWING ORTHODONTIC BRACKET

BACKGROUND OF THE INVENTION

Orthodontic treatment of improperly positioned teeth involves the application of mechanical forces to urge the teeth into correct alignment and orientation. Such treatment typically involves use of orthodontic brackets which are small slotted bodies configured for direct attachment to the front or labial surfaces of the teeth, or alternatively for attachment to bands which are in turn cemented or otherwise secured around the teeth.

A resilient curved arch wire is then seated in the bracket slots, and the arch wire is bent or twisted before installation. The restoring force exerted by the seated resilient wire tends to shift the teeth into orthodontically correct alignment. Depending on the shape of the arch wire (both round and rectangular cross sections are in common use) and the orientation of the bracket slot, it is possible to apply forces which will shift, rotate or tip the teeth in any desired direction.

It is necessary to secure the arch wire in the bracket slot to insure that the wire is not displaced or dislodged when chewing food or brushing the teeth, or by application of other forces by the patient. Brackets are accordingly provided with tie wings which are cleatlike surfaces on opposite sides of the bracket slot, and around which a ligature wire or an elastic band can be anchored by the orthodontist to capture the arch wire in the bracket slot.

Conventional brackets thus have a gingival (gum facing) tie wing, and an occlusal (extending toward the tooth biting edge) tie wing, and known twin brackets have two pairs of such tie wings. More recently introduced brackets are of a triwing configuration with two spaced-apart tie wings on the occlusal side, and a single central tie wing on the gingival side which acts as a fulcrum.

An advantage of this triwing arrangement is that it enables the orthodontist to ligate the arch wire in a fashion which permits rotation of the associated tooth. Another advantage is that the bracket can be tapered (decreased in width gingivally) to match the natural tapered contour of the tooth. Another reason for the conventional triwing arrangement is that the single gingival tie wing, which is usually of relatively small cross section, is positioned away from occlusal forces which might break the wing away from the bracket body.

A disadvantage of conventional triwing brackets is that the two spaced-apart occlusal tie wings are of reduced cross section, and may not have sufficient strength to resist fracture due to occlusal forces. In most cases, breakage of a tie wing will require time-consuming replacement of the entire bracket to insure that the arch wire remains properly seated in the bracket slot. This problem is particularly noticeable in recently introduced brackets made of ceramic material which is brittle and susceptible to fracture upon application of heavy loads to bracket portions of thin cross section.

The bracket of this invention provides improved structural reliability and integrity by departing completely from the conventional triwing design which places the spaced-apart wings on the occlusal side. The improved bracket positions a strong and relatively wide single wing on the occlusal side of the bracket body, and places the spaced-apart wings (needed for rotation control) on the gingival side which is sheltered from heavy occlusal forces.

SUMMARY OF THE INVENTION

Briefly stated, the orthodontic bracket of this invention is a triwing configuration having a single occlusal tie wing, and a pair of spaced-apart gingival tie wings, the occlusal and gingival tie wings being positioned on opposite sides of a generally central arch-wire slot in the bracket. The single occlusal tie wing has a mesiodistal width at least equal to the combined corresponding widths of the gingival tie wings, and is preferably extended along the full width of the bracket. The new tie wing configuration is of particular utility in small mandibular brackets made of brittle materials such as ceramic.

BRIEF DESCRIPTION OF THE DRAWINGS

FIG. 5 is a front elevation of the improved bracket on a mandibular tooth, and ligated with an elastic band for application of rotation force; and FIG. 6 is a top occlusal view of the tooth and ligated bracket shown in FIG. 5.

DESCRIPTION OF THE PREFERRED EMBODIMENT

Figure 1:
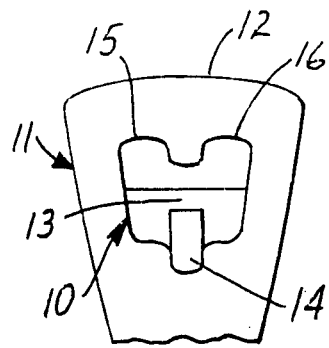
FIG. 1 is a front elevation of a prior-art triwing bracket as mounted on a tooth.

FIG. 1 shows the general concept of a known triwing orthodontic bracket 10 adhesively secured to the front surface of a lower incisor tooth 11 with an occlusal edge 12. The bracket has a central mesiodistally extending arch-wire slot 13, a single gingival tie wing 14, and a pair of spaced-apart occlusal tie wings 15 and 16. As explained above, tie wings 15 and 16 are of reduced cross section as compared to the main bracket body, and present a risk of tie-wing fracture if loaded with heavy occlusal force (e.g., chewing a hard roll).

Figure 2:
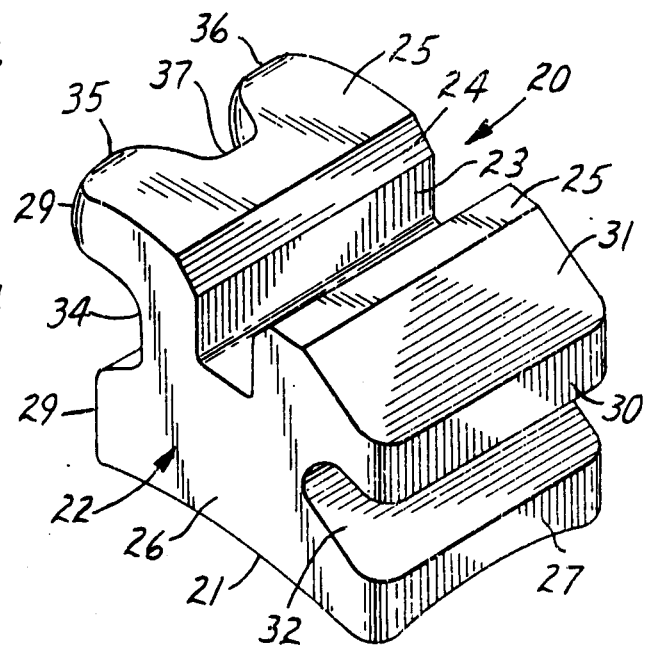
FIG. 2 is a pictorial view of a triwing bracket according to the invention.
Figure 3:
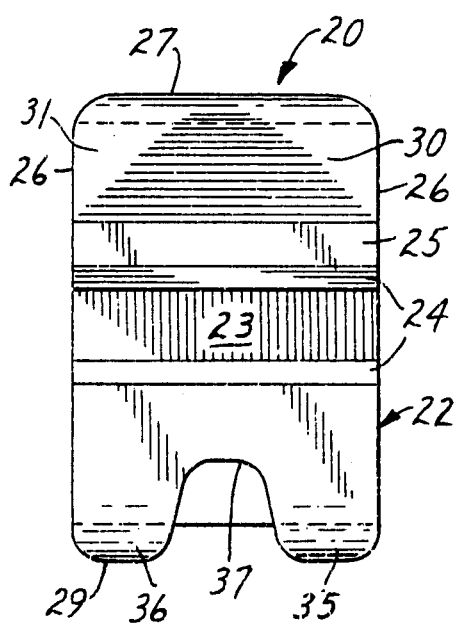
FIG. 3 is a front elevation of the bracket shown in FIG. 2.
Figure 4:
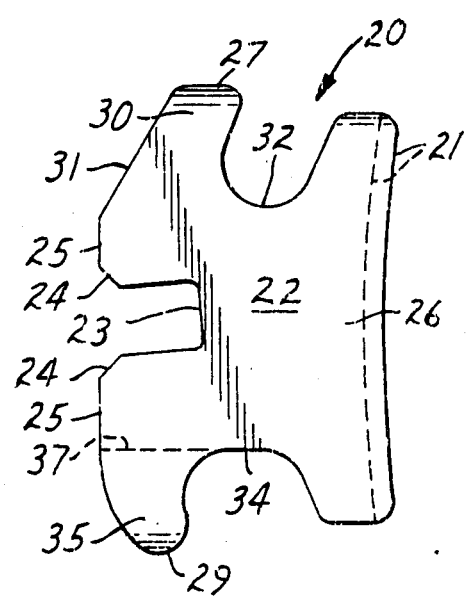
FIG. 4 is a side view of the bracket shown in FIG. 2.

A triwing bracket 20 according to the invention is shown in FIGS. 2–4, and includes a conventional bracket base 21 for cemented attachment to a tooth, and of the usual concave configuration to match the natural convexity of a tooth. A bracket body 22 extends from base 21, and the front of the body defines a mesiodistally extending arch-wire slot 23 with chamfered inlet edges 24. The bracket body has an outer or labial surface 25, opposed side surfaces 26, an occlusal surface 27, and a gingival surface 29.

A full-width occlusal tie wing 30 is defined by bracket body 22 between a front-surface portion 31 which slopes slightly toward the base for compactness, and a mesiodistal notch 32 extending inwardly (i.e., toward the arch-wire slot) from occlusal surface 27. A generally corresponding mesiodistal notch 34 is formed in gingival bracket surface 29 beneath a curved portion of surface 25 (FIG. 4.) to define a pair of gingival tie wings 35 and 36 which are spaced apart by a slot or notch 37 extending from front bracket surface 25 toward base 21.

Occlusal tie wing 30 extends substantially the full width of the bracket body, and has significantly greater structural strength than occlusal tie wings 15 and 16 of the conventional triwing bracket shown in FIG. 1. Gingival tie wings 35 and 36 are of lower strength, but are positioned at the gingival end of the bracket to be sheltered from heavy occlusal forces.

Bracket 20 is shown in FIGS. 5 and 6 as adhesively bonded to a mandibular or lower incisor tooth 40 requiring rotational realignment. A conventional edgewise arch wire 41 is positioned in bracket arch-wire slot 23, and the arch wire is ligated to the bracket by an elastic ligature 42. Ligatures of this style are commercially available (e.g., under the trademark AlastiK from Unitek Corporation), and have the form of a tiny O-ring or donut in an unstressed condition.

Ligature 42 is fully seated under occlusal tie wing 30 in notch 32, but is engaged with only one of the gingival tie wings (36 in FIG. 5) to urge arch wire 41 toward a fully seated position in which the desired rotational correction of tooth 40 will be effected. When rotational movement is not needed, the ligature is fitted under the occlusal and both gingival tie wings. Even in this configuration, the provision of dual small gingival tie wings speeds and simplifies elastic ligature installation, because the tiny elastic O-ring can be first anchored over one small gingival wing and then stretched over the other gingival wing and the occlusal wing.

Bracket 20 is also fully compatible with stainless-steel ligature wires which are in common use in orthodontics. Wire ligatures are usually selected when increased rotational force is needed, but can be engaged with either one or both gingival tie wings (in addition to the occlusal wing) as already explained.

The increased strength of the single wide occlusal tie wing enables the overall bracket mesiodistal width to be decreased (as compared to bracket 10 in FIG. 1) while maintaining adequate structural resistance to tiewing fracture. For example, as compared to a conventional bracket of the style of bracket 10 with a maximum width of about 0.130 inch, bracket 20 can be provided with a significantly decreased width of about 0.100 inch. Reduced bracket width is important due to the narrow width of typical lower central and lateral incisor teeth, because it provides increased interbracket spacing for greater arch-wire flexibility, and because it enables the bracket to be fitted on a badly malrotated tooth.

Bracket 20 is primarily intended for use on the anterior and bicuspid teeth of the lower arch where the tooth width is small and significant rotational corrections are often needed. The increased occlusal tie-wing strength of the new bracket is especially advantageous in brittle ceramic brackets, but the invention can be usefully incorporated in metal or plastic brackets as well. The new triwing configuration is of course also useful in so-called straight-wire brackets and other brackets in which the arch-wire slot is angulated for application of torque or other corrective forces.

There has been described an improved triwing bracket which provides significantly greater occlusal tie-wing strength as compared to known designs, while maintaining all of the triwing advantages dismissed above, and permitting bracket width reduction with improved structural integrity.

What is claimed is:

1. A labial triwing orthodontic bracket comprising a base, a body extending integrally from the base, said body having an outer labial face and having a mesiodistally extending arch-wire slot extending from the labial face toward the base, a pair of spaced-apart ligature tie wings extending gingivally away from the arch-wire slot, and a single tie wing extending occlusally from the arch-wire slot, the single occlusal tie wing having a mesiodistal width at least as large as the combined mesiodistal widths of the spaced-apart gingival tie wings, wherein the width of the occlusal tie wing substantially corresponds to the mesiodistal width of the bracket body and base.

2. A triwing orthodontic bracket comprising a base, a body extending integrally from the base and defining a mesiodistally extending arch-wire slot, a pair of spaced-apart ligature tie wings extending gingivally away from the arch-wire slot, and a single tie wing extending occlusally from the arch-wire slot, the single occlusal tie wing having a mesiodistal width at least as large as the combined mesiodistal widths of the spaced-apart gingival tie wings, wherein the width of the occlusal tie wing substantially corresponds to the mesiodistal width of the bracket body, wherein the base, body and tie wings are integrally formed of a ceramic material, and wherein the width of the bracket body and occlusal tie wing is about 0.100 inch.

3. An integrally formed ceramic orthodontic bracket having a body with an outer labial face, and with a base adapted for attachment to a mandibular tooth; the body defining an arch-wire slot extending from the labial face toward the base, and a pair of mesiodistally extending notches on opposite sides of the arch-wire slot to form occlusal and gingival tie wings for anchorage of a ligature; a gingival end of the body further having a labiolingually extending notch formed between the labial face and the gingival mesiodistally extending notch to divide the gingival tie wing into a pair of spaced-apart gingival tie wings; the occlusal tie wing being continuous and extending along the entire mesiodistal width of the occlusal end of the bracket body, the occlusal tie wing having an outer surface which slopes from the body labial face toward the base.

4. A triwing orthodontic bracket comprising a base, a body extending integrally from the base and defining a mesiodistally extending arch-wire slot, a pair of spaced-apart ligature tie wings extending gingivally away from the arch-wire slot, and a single tie wing extending occlusally from the arch-wire slot, the single occlusal tie wing having a mesiodistal width at least as large as the combined mesiodistal widths of the spaced-apart gingival tie wings, wherein the width of the occlusal tie wing substantially corresponds to the mesiodistal width of the bracket body, and wherein the width of the bracket body and occlusal tie wing is about 0.100 inch.

* * * * *